United States Patent
Davis

(10) Patent No.: US 12,364,703 B2
(45) Date of Patent: *Jul. 22, 2025

(54) HOMOGENEOUS OPHTHALMIC COMPOSITION

(71) Applicant: Randal Davis, Chattanooga, TN (US)

(72) Inventor: Randal Davis, Chattanooga, TN (US)

(*) Notice: Subject to any disclaimer, the term of this patent is extended or adjusted under 35 U.S.C. 154(b) by 0 days.

This patent is subject to a terminal disclaimer.

(21) Appl. No.: 17/707,913

(22) Filed: Mar. 29, 2022

(65) Prior Publication Data

US 2022/0331338 A1 Oct. 20, 2022

Related U.S. Application Data

(63) Continuation of application No. 17/018,040, filed on Sep. 11, 2020, now Pat. No. 11,452,732, which is a continuation-in-part of application No. 16/158,904, filed on Oct. 12, 2018, now Pat. No. 10,780,100, which is a continuation of application No. 14/846,752, filed on Sep. 5, 2015, now Pat. No. 10,130,639.

(51) Int. Cl.
| | |
|---|---|
| *A61K 31/573* | (2006.01) |
| *A61K 9/00* | (2006.01) |
| *A61K 9/08* | (2006.01) |
| *A61K 31/196* | (2006.01) |
| *A61K 31/4709* | (2006.01) |
| *A61K 47/10* | (2017.01) |
| *A61K 47/18* | (2017.01) |
| *A61K 47/38* | (2006.01) |
| *A61P 27/02* | (2006.01) |

(52) U.S. Cl.
CPC .......... *A61K 31/573* (2013.01); *A61K 9/0048* (2013.01); *A61K 9/08* (2013.01); *A61K 31/196* (2013.01); *A61K 31/4709* (2013.01); *A61K 47/10* (2013.01); *A61K 47/183* (2013.01); *A61K 47/38* (2013.01); *A61P 27/02* (2018.01)

(58) Field of Classification Search
CPC .............. A61K 31/196; A61K 31/4709; A61K 31/573; A61K 47/10; A61K 47/183; A61K 47/186; A61K 47/26; A61K 47/38; A61K 9/0048; A61K 9/08; A61P 27/02–14

See application file for complete search history.

(56) References Cited

U.S. PATENT DOCUMENTS

| | | | |
|---|---|---|---|
| 5,607,942 A | 3/1997 | Petersen et al. | |
| 5,800,807 A | 9/1998 | Hu et al. | |
| 6,716,830 B2 | 4/2004 | Cagle et al. | |
| 7,671,070 B2 | 3/2010 | Cagle et al. | |
| 8,129,431 B2 | 3/2012 | Sawa et al. | |
| 8,669,290 B2 | 3/2014 | Sawa et al. | |
| 8,754,131 B2 | 6/2014 | Sawa et al. | |
| 8,871,813 B2 | 10/2014 | Sawa et al. | |
| 10,130,639 B1 * | 11/2018 | Davis | A61K 9/0048 |
| 10,780,100 B2 * | 9/2020 | Davis | A61K 9/0048 |
| 11,452,732 B2 * | 9/2022 | Davis | A61K 9/0048 |
| 2007/0049522 A1 | 3/2007 | Babu | |
| 2007/0087980 A1 | 4/2007 | Suzuki | |
| 2008/0050335 A1 | 2/2008 | Faour | |
| 2011/0082125 A1 | 4/2011 | Singh | |
| 2015/0174105 A1 * | 6/2015 | Hernandez | A61P 27/10 514/397 |

OTHER PUBLICATIONS

"Intrastromal corneal ring segment SK implantation for moderate to severe keratoconus" by Sansanayudh et al., J. Cataract. Refract. Surg. 36, 110-13(2010).
"Update on twice-daily bromfenac sodium sesquihydrate to treat postoperative ocular inflammation following cataract extraction" by Carreno et al., Clin. Opthal. 6, 637-44(2012).
Hayasaka et al., Opthalmic Res. 35, 341-44 (2003) (PubMed Abstract 14688425).
Carreno et al., Clin. Opthalmol. 6, 637-44 (2012) (PubMed Abstract 22570544).
"Opthalmic Antibiotic-Steroid Combinations Review," Mar. 1, 2010, Provider Synergies, LLC, 2004-2010 (7 pgs.).
Shoss et al., "Postoperative Care in Cataract Surgery," vol. 24, No. 1, Jan. 2013, pp. 66-73, www.co-opthalmology.com.
Carreno et al., Clin. Opthalmol 2012; 6:637-644, Apr. 27, 2012.
"Care of the Adult Patient with Cataract: Reference Guide for Clinicians," American Optometric Association, Mar. 1999 (43 pgs.).
Olthoff et al., American Academy of Opthalmology, vol. 112; Jun. 6, 2005.pp. 953-961 and p. 953 el-953 e7.
Donnenfeld et al., Int Opthalmol Clin. 2006 Fall; 46(4):21-40.
Freeman et al., Expert Rev Opthalmol. 2009; 4(1): 59-64 (8 pgs.).
Dry Eye Zone: Preservative Reference List, http://www.dryeyezone.com/encyclopedia/preservativeslist.html, Nov. 18, 2014 (4 pgs.).

* cited by examiner

*Primary Examiner* — Theodore R. Howell
(74) *Attorney, Agent, or Firm* — Eric B. Fugett; Mark A. Pitchford; Pitchford Fugett, PLLC

(57) ABSTRACT

This application is directed to a homogeneous solution of an aqueous, topical composition useful for the treatment of infection and/or for the treatment of inflammation due to trauma to tissue. Specifically, this application relates to a homogeneous, aqueous composition of a quinolone antibiotic and an anti-inflammatory agent.

2 Claims, No Drawings

HOMOGENEOUS OPHTHALMIC COMPOSITION

CROSS-REFERENCES TO RELATED APPLICATIONS

This application is a Continuation of U.S. Non-Provisional patent application Ser. No. 17/018,040, filed Sep. 11, 2020 and titled "Homogeneous Ophthalmic Composition," which is a Continuation-in-Part of U.S. Non-Provisional patent application Ser. No. 16/158,904, filed Oct. 12, 2018 and titled "Homogeneous Ophthalmic Composition," which issued as U.S. Pat. No. 10,780,100 on Sep. 22, 2020 and is a Continuation of U.S. Non-Provisional patent application Ser. No. 14/846,752, filed Sep. 5, 2015 and titled "Homogeneous Ophthalmic Composition," which issued as U.S. Pat. No. 10,130,639 on Nov. 20, 2018, the entire disclosure of each of which is hereby incorporated by reference.

STATEMENT REGARDING FEDERALLY SPONSORED RESEARCH OR DEVELOPMENT

Not Applicable.

REFERENCE TO SEQUENCE LISTING OR COMPUTER PROGRAM LISTING APPENDIX

Not Applicable.

BACKGROUND OF THE INVENTION

A cataract is an opaque portion of the lens of the eye. A cataract can be localized to a small region of the lens or it can be diffuse wherein the entire lens appears cloudy. It is the primary cause of visual impairment worldwide, and also the leading cause of vision loss in the United States. An estimated 20.5 million Americans aged 40 years and older have a cataract in one or both eyes. This number is expected to increase to 30.1 million by 2020.

Cataracts can occur at any age and can be present at birth. Causes of cataracts include age, heredity, trauma, inflammation, metabolic disorders, smoking, alcohol consumption, nutritional deficiencies, certain medications, and ultra-violet radiation. Fortunately, cataract surgery is available to reduce this visual impairment.

Cataract surgery involves removal of the entire eye lens with concomitant replacement of the lens with an artificial lens. According to the WHO, the number of cataract surgeries performed in 2010 was estimated to be around 20 million and this number is expected to reach 32 million by 2020. About 3 million cataract surgeries are performed each year in the U.S. alone, making it the most common surgery for Americans over age 65. The amount spent on cataract surgeries in the U.S. is several billion dollars per year.

Proper post-operative care is critical to ensure an optimal visual outcome after cataract surgery. It is during the period of post-operative care that most complications occur, such as bacterial infection, uncontrolled elevated intraocular pressure (IOP), ocular hypertension, malignant glaucoma, wound leakage, cystoid macular edema (GEM), endophthalmitis, iris prolapse, intraocular lens dislocation, hemorrhage, and severe inflammation. The post-operative regimen normally includes restricted activity and the application of a multitude of topical medications to the eye at numerous times per day for 1-8 weeks depending on the patient's situation and the nature of the surgery. These topical medications generally include an antibiotic to be applied 1-4× per day; a steroidal agent to be applied 1-4× per day, and/or a non-steroidal agent to be applied 1-4× per day, with a 5 minute gap between the application of the each medication to the eye. The time gap between doses helps to diminish the likelihood that the first dose will be washed out by the second dose because of insufficient time for absorption of the first dose.

Most people, especially the elderly who undergo the majority of cataract surgeries, experience difficulty in complying with such a complicated medication regimen. For example, it is difficult for some people to put drops in their eyes, which is amplified by the need to do so four times a day with three separate solutions for a total of 1-8 weeks. As mentioned above, there is a problem wash out of the first medicine by application of the second medicine if the required wait time is not adhered to. Another problem is that one or more of the three bottles may be misplaced, contaminated, or damaged. Yet another problem is the difficulty in keeping track of which medicine was already instilled in the eye when there are three bottles of medicine to be used in one sitting. Still another problem is that the length of time the medicating process takes is long because there is a wait time of 5 minutes after each drop is instilled, which process totals about an hour a day devoted to instilling drops to the eye. Also, another problem is that attempts at combining a quinoline antibiotic with an anti-inflammatory agent results in formulations containing a precipitate and/or particulate matter as in a suspension so that there are none commercially available as an aqueous solution.

Thus, there is an urgent need for an easier-to-follow medication regimen in order to increase patient compliance and to ensure better visual outcomes. The composition described in this application solves this problem by combining all three previously separate medications into a single, homogeneous solution, which will be significantly less complicated for the patient to use and will result in better compliance and visual outcomes.

Unexpectedly, preliminary results indicate that use of the composition described herein, which contains all of the active ingredients within one solution, seems to reduce the incidence of cystoid macular edema (CME) more effectively than the use of separate solutions of each of the active ingredients. CME is the most prevalent cause of vision loss after cataract surgery, with up to 58% of patients having some angiographic evidence of CME and there is no reliable treatment for the prevention or treatment of CME following cataract surgery.

BRIEF SUMMARY

This Brief Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Compositions including an aqueous, homogeneous solution of an antibiotic or mixtures thereof and an anti-inflammatory agent or mixtures thereof are disclosed herein. The pH of the compositions disclosed herein can range from about 4.5 to about 8.5.

In one embodiment, a composition can contain 0.5% by weight moxifloxacin hydrochloride, 0.07% bromfenac sodium sesquihydrate, 0.1% by weight dexamethasone sodium phosphate, 0.01% by weight edetate disodium dihydrate, 0.1% by weight hydroxyethyl cellulose, 0.5% by weight benzalkonium chloride, hydrochloric acid to adjust pH, sodium hydroxide to adjust pH, and 1.8% glycerin.

In another embodiment, a composition can contain 0.5% by weight moxifloxacin, 0.035% bromfenac, 0.1% by weight dexamethasone phosphate, 0.01% by weight edetate disodium dihydrate, hydroxyethyl cellulose to adjust viscosity (e.g., to about 4800 cps), 0.005% by weight/volume ("w/v") benzalkonium chloride (e.g., 50 ml of 1% by weight benzalkonium chloride solution in a 10,000 ml batch), hydrochloric acid to adjust pH, sodium hydroxide to adjust pH, and 1.8% glycerin.

DETAILED DESCRIPTION

The details of one or more embodiments of the presently disclosed subject matter are set forth in this document. Modifications to embodiments described in this document, and other embodiments, will be evident to those of ordinary skill in the art after a study of the information provided herein. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the subject matter disclosed herein.

Unless defined otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices and materials are now described.

The terms "a", "an", and "the" refer to "one or more" when used in this application, including the claims Thus, for example, reference to "a steroid" includes a plurality of particles of the steroid, and so forth. The use of the word "a" or "an" when used in conjunction with the term "comprising" in the claims and/or the specification may mean "one," but it is also consistent with the meaning of "one or more," "at least one," and "one or more than one."

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The compositions and methods of the present disclosure, including components thereof, can comprise, consist of, or consist essentially of the essential elements and limitations of the embodiments described herein, as well as any additional or optional components or limitations described herein or otherwise useful.

The phrase "in one embodiment," as used herein does not necessarily refer to the same embodiment, although it may. Conditional language used herein, such as, among others, "can", "might", "may", "e.g.," and the like, unless specifically stated otherwise, or otherwise understood within the context as used, is generally intended to convey that certain embodiments include, while other embodiments do not include, certain features, elements and/or states.

Unless otherwise indicated, all numbers expressing physical dimensions, quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration, percentage or a physical dimension such as length, width, or diameter, is meant to encompass variations of in some embodiments +−40% or more, in some embodiments +−20%, in some embodiments +−10%, in some embodiments +−5%, in some embodiments +−1%, in some embodiments +−0.5%, and in some embodiments +−0.1% from the specified value or amount, as such variations are appropriate to perform the disclosed methods.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The present invention contemplates an aqueous, homogeneous solution of an antibiotic or mixtures thereof and an anti-inflammatory agent or mixtures thereof. Also contemplated is a method of treatment of an ophthalmic, an otic, or a nasal condition by the topical application of the contemplated solution to the affected tissue. The indicated condition may be an infection or an inflammation of tissue or may be for the prevention of post-surgical trauma or infection, i.e., a prophylactic measure. Another contemplated embodiment is a method of making the contemplated solution.

In one embodiment, the solution contains one antibiotic and one anti-inflammatory agent. In another embodiment, the solution contains a mixture of antibiotics and one anti-inflammatory agent. In yet another embodiment, the solution contains one antibiotic and a mixture of anti-inflammatory agents. In still yet another embodiment, the solution contains a mixture of antibiotics and a mixture of anti-inflammatory agents.

The contemplated solution is an aqueous, homogeneous solution and not a suspension. As is generally understood, a solution denotes a homogeneous, transparent liquid that is free of particulate matter, and a suspension denotes an aqueous formulation that contains solid particles and is not homogeneous.

Quite often, the combination of an antibiotic and an anti-inflammatory agent results in precipitate formation so that antibiotic-steroid combinations currently available are in the form of ointments and suspensions. However, both of these forms of medication are problematic for treatment of the eyes in particular. Ophthalmic ointments are cumbersome to use, do not deliver consistent levels of medication, and can impede delivery of other ophthalmic drugs by serving as a physical and chemical barrier due to the presence of the viscous gel vehicle. Ophthalmic suspensions require adequate agitation before each use, do not deliver consistent levels of medication, mix with tears less rapidly, and can cause irritation due to the presence of particulates. Also, absorption of both of these forms of medication is minimal.

The concentrations of the antibiotic and the anti-inflammatory agent in the solution will vary depending upon the activity of the particular antibiotic and the nature of the treatment, i.e., infection or prophylactic. In one embodiment, the composition contains about 0.1 to about 1% by weight of the antibiotic or mixtures thereof and about 0.01 to about 1% by weight of the anti-inflammatory agent or mixtures thereof. In another embodiment, the composition contains about 0.5 to about 1% by weight of the antibiotic or mixtures thereof and about 0.1 to about 1% by weight of the anti-inflammatory agent or mixtures thereof. In still another embodiment, the composition contains about 0.5% by weight of the antibiotic or mixtures thereof and about 0.1% by weight of the anti-inflammatory agent or mixtures thereof. When there are mixtures of anti-inflammatory agents in the composition, each of them is present in the range of about 0.07 to about 1% by weight. The pH of the composition ranges from about 4.5 to about 8.5. The pH of the composition can also be from 7.5-8.5. In some embodiments, the pH of the final composition can be from about 8.20 to about 8.25.

The present composition contains a quinolone antibiotic, derivatives thereof, salts thereof, or mixtures thereof. Quinolone antibiotics include moxifloxacin, ciprofloxacin, oflaxacin, norfloxacin, lomefloxecin, derivatives thereof, salts thereof, and mixtures thereof. In another embodiment, the antibiotic is moxifloxacin hydrochloride.

The composition also contains an anti-inflammatory agent. Anti-inflammatory agents include a non-steroidal agent, a steroidal agent, or a mixture of a non-steroidal agent and a steroidal agent. In one embodiment, the anti-inflammatory agent comprises a steroidal agent. Common steroidal agents include dexamethasone sodium phosphate, budensonide, triamcinolone, hydrocortisone, loteprednol, prednisolone, mometasone, fluticasone, rimexolone, fluorometholone, beclomethasone, flunisolide, derivatives thereof, and mixtures thereof. In yet another embodiment, the anti-inflammatory agent is dexamethasone sodium phosphate.

In an alternative embodiment, the anti-inflammatory agent comprises a non-steroidal agent. Well-known non-steroidal agents include bromfenac, bromfenac sodium, bromfenac sodium sesquihydrate, aspirin, nabumetome, etodolac, meclofenamate, ibuprofen, flurbiprofen, diffusional, piroxicam, suprofen, diclofenac, sulindac, oxyphenbutazone, oxaproazin, ketorolac, naproxen, nepafenac, bromfenac, mefamic acid, ketoprofen, amfenac, fenoprofen, phenylbutazone, indomethacin, cececoxib, nupafant, filaminast, salts thereof, hydrates thereof, and derivatives thereof. In one embodiment, the anti-inflammatory agent is bromfenac or a pharmaceutically acceptable salt thereof or a hydrate thereof or mixtures thereof. In another embodiment, the anti-inflammatory agent is bromfenac sodium sesquihydrate. In yet another embodiment, the anti-inflammatory agent is bromfenac sodium.

In a different embodiment, the anti-inflammatory agent is a mixture of a non-steroidal agent and a steroidal agent. For example, the anti-inflammatory agent can be a mixture of bromfenac sodium and dexamethasone sodium phosphate. As another example, the anti-inflammatory agent is a mixture of bromfenac sodium sesquihydrate and dexamethasone sodium phosphate.

Thus, one embodiment of the composition can be moxifloxacin hydrochloride and dexamethasone sodium phosphate. Another embodiment of the composition can be moxifloxacin hydrochloride and bromfenac sodium. Yet another embodiment can be moxifloxacin hydrochloride, bromfenac sodium sesquihydrate, and dexamethasone sodium phosphate.

The composition further can contain a pharmaceutically acceptable additive. This additive can be a preservative, a solubility enhancer, a thickener, a pH moderating agent, a buffer, a humectant, or mixtures thereof. Commonly known preservatives are contemplated herein, including a detergent preservative, an oxidizing preservative, and an ionic-buffered preservative. Examples of preservatives are edetate sodium; benzalkonium chloride; centrimonium chloride; sodium perborate; stabilized oxychlorocomplex; sorbic acid; thimersol; polyquarternium-1; polyhexamethylene biguanide; chlorobutanol; phenylethyl alcohol; methyl paraben; propyl paraben; a combination of boric acid, zinc, sorbital, and propylene glycol; and mixtures thereof.

The composition can also contain a solubility enhancer. Common solubility enhancers include cyclodextrin, polysorbate 20, polysorbate 60, polysorbate 80, Pluronic®, and mixtures thereof.

The present composition can also include a thickener. Examples of thickeners include hydroxyethyl cellulose, methyl cellulose, hydroxypropylmethyl cellulose, carboxymethyl cellulose, hydroxypropyl cellulose, polyvinyl alcohol, polyvinylpyrrolidone, and mixtures thereof.

The composition can contain a pH moderating agent. Suitable pH moderating agents are acids and bases such as sodium hydroxide, hydrochloric acid, phosphoric acid, acetic acid, and mixtures thereof.

Buffers can also be included in the composition. Appropriate buffers include boric acid, sodium borate, and mixtures thereof.

Furthermore, the composition can contain a humectant. The humectant can be glycerin, sorbitol, gelatin, mannitol, dextrose, sucrose, urea, and mixtures thereof.

Also contemplated herein is a composition comprising moxifloxacin hydrochloride, dexamethasone sodium phosphate, edetate disodium dihydrate, hydroxyethyl cellulose, benzalkonium chloride, hydrochloric acid to adjust pH, sodium hydroxide to adjust pH, and glycerin.

A composition including 0.5% by weight moxifloxacin hydrochloride, 0.08% by weight bromfenac sodium, 0.1% by weight dexamethasone sodium phosphate, 0.01% by weight edetate disodium dihydrate, 0.1% by weight hydroxyethyl cellulose, 0.5% by weight benzalkonium chloride, hydrochloric acid to adjust pH, sodium hydroxide to adjust pH, and 1.8% by weight glycerin is contemplated herein.

Also, a composition containing 0.5% by weight moxifloxacin hydrochloride, 0.07% bromfenac sodium sesquihydrate, 0.1% by weight dexamethasone sodium phosphate, 0.01% by weight edetate disodium dihydrate, 0.1% by weight hydroxyethyl cellulose, 0.5% by weight benzalkonium chloride, hydrochloric acid to adjust pH, sodium hydroxide to adjust pH, and 1.8% glycerin is contemplated herein.

In addition, a composition containing 0.5% by weight moxifloxacin hydrochloride, 0.1% by weight dexamethasone sodium phosphate, 0.01% edetate disodium dihydrate, 0.1% by weight hydroxyethyl cellulose, 0.5% by weight benzalkonium chloride, hydrochloric acid to adjust pH, sodium hydroxide to adjust pH, and 1.8% by weight glycerin is considered here.

Another composition including 0.035% by weight bromfenac sodium, 0.1% by weight dexamethasone sodium phosphate, 0.01% by weight edetate disodium dihydrate, hydroxyethyl cellulose (4,800 cps) to adjust viscosity, 0.005% w/v benzalkonium chloride, hydrochloric acid to adjust pH, sodium hydroxide to adjust pH, 1.8% by weight glycerin, and 0.05% by weight polysorbate 80 is contemplated herein.

Yet another composition containing 0.5% by weight moxifloxacin hydrochloride, 0.035% bromfenac sodium sesquihydrate, 0.1% by weight dexamethasone sodium phosphate, 0.01% by weight edetate disodium dihydrate, hydroxyethyl cellulose (4,800 cps) to adjust viscosity, 0.005% w/v benzalkonium chloride, hydrochloric acid to adjust pH, sodium hydroxide to adjust pH, 1.8% glycerin, and 0.05% by weight polysorbate 80 is contemplated herein.

Still yet another composition containing 0.5% by weight moxifloxacin hydrochloride, 0.1% by weight dexamethasone sodium phosphate, 0.01% edetate disodium dihydrate, hydroxyethyl cellulose (4,800 cps) to adjust viscosity, 0.005% by weight benzalkonium chloride, hydrochloric acid to adjust pH, sodium hydroxide to adjust pH, and 1.8% by weight glycerin is contemplated here.

The composition can be designed for a range of osmolalities though iso-osmolal is the norm. Osmolalities range from about 175 to about 330 mOsm/kg. In one embodiment, the osmolality ranges from 280 to 325 mOsm/kg. The osmolality can be adjusted by the addition of salt such as sodium chloride or potassium chloride or by the use of monosaccharides.

Furthermore, a method of treating an ophthalmic infection or inflammation is contemplated herein. One embodiment of the method entails topically applying an aqueous, homogeneous solution made of an antibiotic or mixtures thereof and an anti-inflammatory agent or mixtures thereof to the eye. In one embodiment, the antibiotic is moxifloxacin hydrochloride and the anti-inflammatory agent is dexamethasone sodium phosphate. In another embodiment, the antibiotic is moxifloxacin hydrochloride and the anti-inflammatory agent is bromfenac sodium. In yet another embodiment, the antibiotic is moxifloxacin hydrochloride and the anti-inflammatory agent is a mixture of bromfenac sodium and dexamethasone sodium phosphate. The aqueous, homogeneous solution of an antibiotic or mixtures thereof and an anti-inflammatory agent or mixtures thereof can be applied topically to the eye once a day, twice a day, three times a day, or four times a day as needed with variable durations of therapy ranging from 1-8 weeks or longer.

Moreover, a method of making an ophthalmic solution is contemplated herein. One embodiment of the method entails dissolving moxifloxacin, dexamethasone, and sodium bromfenac each in separate receptacles of water with stirring to form three aqueous compositions; the pH of each of the compositions is adjusted to pH 7.5-8.5; then hydroxyethyl cellulose is added to the dexamethasone composition with stirring, followed by the addition of glycerin to the dexamethasone composition with stirring; followed by the addition of benzalkonium chloride to the dexamethasone composition with stirring; followed by the addition of edetate disodium to the dexamethasone composition with stirring. The pH is adjusted to pH 7.5-8.5. Next, the dexamethasone composition is added to the moxifloxacin composition to form a dexamethasone and moxifloxacin composition; then, the sodium bromfenac composition is added to the dexamethasone and moxifloxacin composition with stirring. In an alternative embodiment, sodium bromfenac sesquihydrate can be substituted for sodium bromfenac.

Another embodiment of the method entails dissolving moxifloxacin, dexamethasone, and sodium bromfenac each in separate receptacles of water with stirring to form three aqueous compositions; the pH of each of the compositions is adjusted to pH 8.20-8.25; then edetate disodium is added to the dexamethasone composition with stirring, followed by the addition of glycerin to the dexamethasone composition with stirring; followed by the addition of hydroxyethyl cellulose (4,800 cps) to the dexamethasone composition with stirring. The pH is adjusted to pH 8.20-8.25. Next, polysorbate 80 is added to the bromfenac composition with stirring and then adjust the pH to 8.20-8.25, then the bromfenac composition is added to the moxifloxacin composition to form a bromfenac and moxifloxacin composition; then, the dexamethasone composition is added to the bromfenac and moxifloxacin composition with stirring to form a dexamethasone and bromfenac and moxifloxacin composition. In an alternative embodiment, sodium bromfenac sesquihydrate can be substituted for sodium bromfenac. Finally, benzalkonium chloride is added to the solution of dexamethasone and bromfenac and moxifloxacin with stirring.

In another method, moxifloxacin and dexamethasone are dissolved in separate receptacles of water with stirring to form two aqueous compositions; the pH of each of the compositions is adjusted to pH 7.5-8; then hydroxyethyl cellulose is added to the dexamethasone composition with stirring, followed by the addition of glycerin to the dexamethasone composition with stirring; followed by the addition of benzalkonium chloride to the dexamethasone composition with stirring; followed by the addition of edetate disodium to the dexamethasone composition with stirring. Next, the dexamethasone composition is added to the moxifloxacin composition to form a dexamethasone-moxifloxacin composition.

In yet another method, moxifloxacin and dexamethasone are dissolved in separate receptacles of water with stirring to form two aqueous compositions; the pH of each of the compositions is adjusted to pH 8.20-8.25; then edetate disodium is added to the dexamethasone composition with stirring, followed by the addition of glycerin to the dexamethasone composition with stirring, and then hydroxyethyl cellulose (4,800 cps) is added to the dexamethasone composition with stirring. Next, the dexamethasone composition is added to the moxifloxacin composition to form a dexamethasone-moxifloxacin composition. Finally, benzalkonium chloride is added to the solution of dexamethasone-moxifloxacin composition with stirring. The final pH is adjusted as needed to 8.20-8.25.

The order of addition of the additives can be varied and what solution they are added to can be varied also as long as the pH of the solution containing the active ingredients is from 7.5 to 8.5 and the pH of the final solution is from 7.5 to 8.5.

EXAMPLES

Example 1

The following procedure was followed to make a homogeneous, aqueous solution of moxifloxacin, sodium bromfenac sesquihydrate, and dexamethasone sodium phosphate.

| Ingredients | Amount |
|---|---|
| Moxifloxacin hydrochloride powder | 5.454 g |
| Bromfenac sodium sesquihydrate powder | 0.4025 g |
| Dexamethasone sodium phosphate powder | 1.1 g |

-continued

| Ingredients | Amount |
| --- | --- |
| Edetate disodium dihydrate powder | 0.1 g |
| Hydroxyethyl cellulose powder (4,800 cps) | 1 g |
| Benzalkonium chloride solution (0.5%/ml) | 5 ml |
| Polysorbate 80 | 0.5 ml |
| Glycerin | 18.2 ml |
| Hydrochloric acid (10% solution) for pH adjustment | varies |
| Sodium hydroxide (1% solution) for pH adjustment | varies |
| Sterile water | up to 1000 ml |

Preliminary attempts to combine the dry active ingredients moxifloxacin and sodium bromfenac and dexamethasone into one aqueous solution by dissolving in water resulted in solubility problems. The resulting mixture appeared hazy with particles visible to the naked eye, where the particles settled on the bottom of the receptacle.

Therefore, the active ingredients moxifloxacin hydrochloride, sodium bromfenac, and dexamethasone sodium phosphate, were weighed out separately and placed into individual clear receptacles. About 300 ml sterile water was added to each receptacle with stirring. All three active ingredients dissolved well to form three transparent solutions. The pH of each of the solutions was then adjusted to pH 7.7-8.5 with hydrochloric acid or sodium hydroxide dropwise. Next, edetate disodium was added to the dexamethasone composition with stirring; followed by the addition of glycerin to the dexamethasone composition with stirring; followed by the addition of hydroxyethyl cellulose (4,800 cps) to the dexamethasone composition with stirring. The pH of the dexamethasone composition was adjusted to pH 8.2. Polysorbate 80 was then added to the bromfenac composition with stirring and the pH of the bromfenac composition was adjusted as needed to pH 8.2. The bromfenac composition containing polysorbate 80 was then added to the moxifloxacin composition to form a bromfenac and moxifloxacin composition. The pH of the bromfenac and moxifloxacin composition was adjusted as needed to pH 8.2. The dexamethasone composition was then added to the bromfenac and moxifloxacin composition with stirring to form a dexamethasone and bromfenac and moxifloxacin composition. The pH of the dexamethasone and bromfenac and moxifloxacin composition was adjusted as needed to pH 8.2. Last, the benzalkonium chloride was added to the solution of dexamethasone and bromfenac and moxifloxacin with stirring, and the pH again adjusted as needed to pH 8.2. The volume was brought up to 1000 ml with sterile water. The solution was clear and transparent. The solution was aseptically filtered and placed into 5 ml sterile droptainers. Testing such as rapid scan for sterility, pyrogenicity, and potency were carried out.

Example 2

The following procedure was followed to make a homogeneous, aqueous solution of moxifloxacin and dexamethasone.

| Ingredients | Amount |
| --- | --- |
| Moxifloxacin hydrochloride powder | 5.454 g |
| Dexamethasone sodium phosphate powder | 1.1 g |
| Edetate disodium dihydrate powder | 0.1 g |
| Hydroxyethyl cellulose powder (4,800 cps) | 1 g |

-continued

| Ingredients | Amount |
| --- | --- |
| Benzalkonium chloride solution (0.5%/ml) | 5 ml |
| Glycerin | 18.2 ml |
| Hydrochloric acid (10% solution) for pH adjustment | varies |
| Sodium hydroxide (1% solution) for pH adjustment | varies |
| Sterile water | up to 1000 ml |

The active ingredients moxifloxacin hydrochloride and dexamethasone sodium phosphate were weighed out separately and placed into individual clear receptacles. About 300 ml sterile water was added with stirring. Both active ingredients dissolved well to form transparent solutions. The pH of each of the solutions was then adjusted to pH 7.7-8.5 with hydrochloric acid or sodium hydroxide dropwise. Next, edetate disodium dehydrate was added to the dexamethasone solution with stirring, followed by the addition of glycerin with stirring, followed by the addition of hydroxyethyl cellulose (4,800 cps) with stirring. The pH was adjusted to 8.2 as needed. This dexamethasone solution was then added to the moxifloxacin solution with stirring to form a moxifloxacin and dexamethasone solution. Last, the benzalkonium chloride solution was added to the moxifloxacin and dexamethasone solution with stirring. The pH was adjusted to 8.2-8.25 as needed. The volume was then brought up to 1000 ml with sterile water. The solution was clear and transparent. The solution was aseptically filtered and placed into 5 ml sterile droptainers. Testing such as rapid scan for sterility, pyrogenicity, and potency were carried out.

Example 3

The following procedure was followed to make a homogeneous, aqueous solution of sodium bromfenac sesquihydrate and dexamethasone sodium phosphate.

| Ingredients | Amount |
| --- | --- |
| Polysorbate 80 liquid | 0.5 ml |
| Bromfenac sodium sesquihydrate powder | 0.4025 g |
| Dexamethasone sodium phosphate powder | 1.1 g |
| Edetate disodium dihydrate powder | 0.1 g |
| Hydroxyethyl cellulose powder (4,800 cps) | 1 g |
| Benzalkonium chloride solution (0.5%/ml) | 5 ml |
| Glycerin | 18.2 ml |
| Hydrochloric acid (10% solution) for pH adjustment | varies |
| Sodium hydroxide (1% solution) for pH adjustment | varies |
| Sterile water | up to 1000 ml |

Preliminary attempts to combine the dry active ingredients sodium bromfenac sesquihydrate and dexamethasone into one aqueous solution resulted in significant solubility issues. The resulting mixture appeared hazy with significant particles visible to the naked eye, which settled on the bottom of the receptacle.

Therefore, the active ingredients were weighed out separately and placed into individual clear receptacles. About 300 ml sterile water was added with stirring. Both active ingredients dissolved well to form two transparent solutions. The pH of each of the solutions was then adjusted to pH 7.7-8.5 with hydrochloric acid or sodium hydroxide dropwise. Next, edetate disodium dehydrate was added to the dexamethasone solution with stirring, followed by the addition of glycerin and hydroxyethyl cellulose (4,800 cps), each with stirring afterwards. The pH of each of the solutions was then adjusted to pH 7.7-8.5 with hydrochloric acid or sodium hydroxide dropwise. The resulting dexamethasone solution was then added to the bromfenac sodium sesquihydrate solution with polysorbate 80 and stirring to form a bromfenac and dexamethasone solution. The pH was adjusted to 8.20-8.25 as needed. Next, the benzalkonium chloride solution was added to the bromfenac-dexamethasone solution. The pH was again adjusted to 8.20-8.25 as needed. The volume was brought up to 1000 ml with sterile water. The solution was clear and transparent. The solution was aseptically filtered and placed into 5 ml sterile droptainers. Testing such as rapid scan for sterility, pyrogenicity, and potency were carried out.

Example 4

The solutions were analyzed by LCMS and standard curve analysis to confirm the identity and quantity of each active ingredient and are summarized below. Separate stock solutions of moxifloxacin HCl, dexamethasone, and sodium bromfenac were used as standards. Three different samples of solutions containing the three active ingredients, i.e., moxifloxacin HCl, dexamethasone, and sodium bromfenac were analyzed for the concentration of moxifloxacin in solution, the concentration of dexamethasone in solution, and the concentration of sodium bromfenac in solution.

| Concentration in Solution | |
|---|---|
| moxifloxacin HCl | 5.458 ± 0.211 mg/ml |
| dexamethasone sodium phosphate | 1.102 + 0.011 mg/ml |
| bromfenac sodium | 0.0405 + 0.047 mg/ml |

Example 5

The pre-treatment regimen for patients who will undergo cataract surgery is one drop applied to the eye per day for each of three days immediately prior to surgery. The post-treatment regimen is one drop applied to the eye four times a day for twenty days, including the day of surgery. In some cases, patients have continued the post-treatment regimen for an additional seven days. In one clinical trial, the use of the composition of the present application appears to have eliminated the incidence of CME, which is one of the most severe complications following cataract surgery.

Although embodiments of the present invention have been described in detail, it will be understood by those skilled in the art that various modifications can be made therein without departing from the spirit and scope of the invention as set forth in the appended claims.

This written description uses examples to disclose the invention and also to enable any person skilled in the art to practice the invention, including making and using any compositions and performing any incorporated methods. The patentable scope of the invention is defined by the claims, and may include other examples that occur to those skilled in the art. Such other examples are intended to be within the scope of the claims if they have elements that do not differ from the literal language of the claims, or if they include equivalent elements with insubstantial differences from the literal languages of the claims.

It will be understood that the particular embodiments described herein are shown by way of illustration and not as limitations of the invention. The principal features of this invention may be employed in various embodiments without departing from the scope of the invention. Those of ordinary skill in the art will recognize numerous equivalents to the specific procedures described herein. Such equivalents are considered to be within the scope of this invention and are covered by the claims.

All of the compositions and/or methods disclosed and claimed herein may be made and/or executed without undue experimentation in light of the present disclosure. While the compositions and methods of this invention have been described in terms of the embodiments included herein, it will be apparent to those of ordinary skill in the art that variations may be applied to the compositions and/or methods and in the steps or in the sequence of steps of the method described herein without departing from the concept, spirit, and scope of the invention. All such similar substitutes and modifications apparent to those skilled in the art are deemed to be within the spirit, scope, and concept of the invention as defined by the appended claims.

Thus, although there have been described particular embodiments of the present invention, it is not intended that such references be construed as limitations upon the scope of this invention except as set forth in the following claims.

What is claimed is:

1. An ophthalmic composition comprising an aqueous, homogeneous solution of a quinolone antibiotic, a steroidal anti-inflammatory agent, a non-steroidal anti-inflammatory agent, edetate disodium dihydrate, hydroxyethyl cellulose, benzalkonium chloride, a pH moderating agent, and a humectant, wherein:
   the quinolone antibiotic is present in an amount of about 0.1 to about 1% by weight;
   the steroidal anti-inflammatory agent is present in an amount of about 0.01 to about 1% by weight;
   the non-steroidal anti-inflammatory agent is present in an amount of about 0.01 to about 1% by weight;
   the quinolone antibiotic is moxifloxacin, a salt thereof, a derivative thereof, or a mixture thereof;
   the steroidal anti-inflammatory agent is selected from the group consisting of dexamethasone, budensonide, triamcinolone, hydrocortisone, loteprednol, prednisolone, mometasone, fluticasone, rimexolone, fluorometholone, beclomethasone, flunisolide, salts thereof, derivatives thereof, and mixtures thereof;
   the non-steroidal anti-inflammatory agent is selected from the group consisting of bromfenac, aspirin, nabumetome, etodolac, meclofenamate, ibuprofen, flurbiprofen, diffusional, piroxicam, suproprofen, diclofenac, sulindac, oxyphenbutazone, oxaproazin, ketorolac, naproxen, nepafenac, mefamic acid, ketoprofen, amfenac, fenoprofen, phenylbutazone, indomethacin, cececoxib, nupafant, filaminast, salts thereof, derivatives thereof, hydrates thereof, and mixtures thereof; and
   the solution has a pH in the range of about 4.5 to about 8.5 and remains a solution during topical application to an eye of a patient.

2. A method of treating or preventing ophthalmic infection or inflammation comprising topically applying the composition of claim 1 to the eye.

* * * * *